(12) United States Patent
Yu (10) Patent No.: US 11,097,813 B2
(45) Date of Patent: Aug. 24, 2021

(54) UNMANNED SURFACE VEHICLE FOR AQUATIC ECOSYSTEM MONITORING AND RESTORATION AND CONTROL METHOD FOR AQUATIC ECOSYSTEM RESTORATION

(71) Applicant: CAS (HEFEI) INSTITUTE OF TECHNOLOGY INNOVATION, Anhui (CN)

(72) Inventor: Daoyang Yu, Anhui (CN)

(73) Assignee: CAS (HEFEI) INSTITUTE OF TECHNOLOGY INNOVATION, Anhui (CN)

( * ) Notice: Subject to any disclaimer, the term of this patent is extended or adjusted under 35 U.S.C. 154(b) by 0 days.

(21) Appl. No.: 16/764,228

(22) PCT Filed: Mar. 11, 2019

(86) PCT No.: PCT/CN2019/077604
§ 371 (c)(1),
(2) Date: May 14, 2020

(87) PCT Pub. No.: WO2020/133709
PCT Pub. Date: Jul. 2, 2020

(65) Prior Publication Data
US 2021/0221479 A1    Jul. 22, 2021

(30) Foreign Application Priority Data

Dec. 27, 2018   (CN) .......................... 201811610135.4

(51) Int. Cl.
   *B63B 35/00*      (2020.01)
   *G01N 21/84*      (2006.01)
   *G01N 33/18*      (2006.01)

(52) U.S. Cl.
   CPC ............. *B63B 35/00* (2013.01); *G01N 21/84* (2013.01); *G01N 33/18* (2013.01); *B63B 2035/006* (2013.01)

(58) Field of Classification Search
   CPC .. B63B 35/00; B63B 2035/006; G01N 21/84; G01N 33/18
   See application file for complete search history.

(56) References Cited

FOREIGN PATENT DOCUMENTS

| CN | 101923764 A | 12/2010 |
|---|---|---|
| CN | 103970093 A | 8/2014 |

(Continued)

OTHER PUBLICATIONS

Machine translation of CN207510670U. (Year: 2018).*
Machine translation of 108674589. (Year: 2018).*

*Primary Examiner* — Jennifer Wecker
*Assistant Examiner* — Kathryn Elizabeth Limbaugh
(74) *Attorney, Agent, or Firm* — Nath, Goldberg & Meyer; Joshua B. Goldberg (57) ABSTRACT

The present invention discloses an Unmanned Surface Vehicle (USV) for aquatic ecosystem monitoring and restoration and a control method for aquatic ecosystem restoration. A control cabin, a water-quality monitoring cabin, and a water treatment equipment compartment are arranged inside a cabin of a hull of the USV for aquatic ecosystem monitoring and restoration, and a water-surface photographing device and a remote communications device are arranged outside the cabin; the control cabin is connected to the water-quality monitoring cabin, the water-surface photographing device, and the water treatment equipment compartment; the water quality parameters include five conventional water quality parameters and eutrophication-based water quality parameters; and the remote communications device is connected to the water-quality monitoring cabin and the water treatment equipment compartment. The pres- (Continued)

ent invention can implement real-time, automatic, and dynamic aquatic ecosystem monitoring, early warning of the water pollution, and self-adaptive ecological restoration based on an artificial intelligent control algorithm.

20 Claims, 2 Drawing Sheets

(56) References Cited

FOREIGN PATENT DOCUMENTS

| | | |
|---|---|---|
| CN | 105242023 A | 1/2016 |
| CN | 107021188 | 8/2017 |
| CN | 207510670 U | 6/2018 |
| CN | 108674589 A | 10/2018 |

* cited by examiner

UNMANNED SURFACE VEHICLE FOR AQUATIC ECOSYSTEM MONITORING AND RESTORATION AND CONTROL METHOD FOR AQUATIC ECOSYSTEM RESTORATION

This is a National Phase Application filed under 35 U.S.C. 371 as a national stage of PCT/CN2019/077604, filed Mar. 11, 2019, and claims priority from Chinese Application No. 201811610135.4, filed Dec. 27, 2018, the content of each of which is hereby incorporated by reference in its entirety.

TECHNICAL FIELD

The present invention relates to the technical field of aquatic ecosystem monitoring and restoration, and in particular, to an Unmanned Surface Vehicle (USV) for aquatic ecosystem monitoring and restoration and a control method for aquatic ecosystem restoration.

BACKGROUND

In China, there is a severe shortage of fresh water resources, and the limited water resources are also suffered from ecosystem deterioration and pollution. Usually, sewage interception, desilting, and water renewal are currently adopted for restoration and treatment of the aquatic ecosystem, especially the treatment of black-odor rivers. This method can only make water look better in a short time, but cannot essentially resolve the problem. The key of water pollution control lies in greatly improving the self-purification capacity of water, to form a complete self-restoring ecosystem for water.

At present, existing water pollution control technologies in China still have the following shortcomings: (1) Existing methods for aquatic ecosystem health monitoring and evaluation are mainly conducted by manual sampling and analysis, which is difficult to dynamically control the water pollution process and development trend in time. (2) Existing methods for water pollution control are basically lagging behind and intrusive in implementation, which is difficult to intervene and treat water pollution earlier. (3) Current water pollution treatment is basically carried out by using single technologies. Accordingly, it is difficult to associate and systematize existing technologies and methods, and hard to realize intelligence and automation. Therefore, it is urgently needed to develop a device that can implement real-time automatic monitoring and restoration of the aquatic ecosystem.

SUMMARY

On this basis, it is necessary to provide an Unmanned Surface Vehicle (USV) for aquatic ecosystem monitoring and restoration and a control method for aquatic ecosystem restoration. This can implement real-time automatic monitoring and restoration of the aquatic environment, and can prevent and control the water pollution earlier.

To achieve the above purpose, the present invention provides the following technical solutions:

A USV for aquatic ecosystem monitoring and restoration includes a hull, a control cabin, a water-quality monitoring cabin, a water-surface photographing device, a water treatment equipment compartment, and a remote communications device, where the control cabin, the water-quality monitoring cabin, and the water treatment equipment compartment are arranged inside a cabin of the hull, and the water-surface photographing device and the remote communications device are arranged outside the cabin; and the control cabin is connected to the water-quality monitoring cabin, the water-surface photographing device, and the water treatment equipment compartment; the water-quality monitoring cabin is configured to monitor water quality parameters of to-be-detected water and obtain an underwater creature image; the water-surface photographing device is configured to obtain a water-surface creature image; the water quality parameters include five conventional water quality parameters and eutrophication-based water quality parameters; the eutrophication-based water quality parameters include chlorophyll content, blue-green algae content, nitrogen content, phosphorus content, and organic pollutant content; the control cabin is configured to receive the water quality parameters, the underwater creature image, and the water-surface creature image, and control the water treatment equipment compartment to restore the to-be-detected water; and the remote communications device is connected to both the water-quality monitoring cabin and the water treatment equipment compartment, and is configured to remotely send obtained data.

Optionally, the water-quality monitoring cabin includes:

an aquatic ecosystem analyzer, connected to the control cabin and configured to monitor the water quality parameters of the to-be-detected water; and an underwater camera, connected to the control cabin and configured to photograph underwater creatures in the to-be-detected water to obtain an underwater creature image.

Optionally, the aquatic ecosystem analyzer includes:

a five-parameter water quality analyzer, configured to monitor the five conventional water quality parameters of the to-be-detected water, where the five conventional water quality parameters include a dissolved oxygen concentration, pH, temperature, turbidity, and conductivity;

a chlorophyll analyzer, configured to monitor chlorophyll content of the to-be-detected water;

a blue-green algae analyzer, configured to monitor blue-green algae content of the to-be-detected water;

a COD analyzer, configured to monitor COD content of the to-be-detected water;

an ammonia-nitrogen analyzer, configured to monitor ammonia nitrogen content of the to-be-detected water;

a total phosphorus analyzer, configured to monitor total phosphorus content of the to-be-detected water; and a total nitrogen analyzer, configured to monitor total nitrogen content of the to-be-detected water.

Optionally, the water treatment equipment compartment includes:

an oxygen aerator, connected to the control cabin and configured to provide oxygen gas for the to-be-detected water through micro-nano or conventional aeration;

an automatic water treatment agent feeding device, connected to the control cabin and configured to feed a water treatment agent to the to-be-detected water; and an automatic water treatment bacteria feeding device, connected to the control cabin and configured to feed water treatment bacteria to the to-be-detected water.

Optionally, the USV for aquatic ecosystem monitoring and restoration further includes:

a power equipment compartment, arranged inside the cabin and configured to drive the hull; and a solar panel, connected to the power equipment compartment, arranged on the outer surface of the cabin, and configured to charge equipment in the power equipment compartment.

Optionally, the power equipment compartment includes a generator, a lithium battery pack, a hybrid power control device, a control cabinet, a frequency converter, an alternating-current motor, a decelerator, and a propeller; and the hybrid power control device is connected to both the generator and the lithium battery pack, and is configured to control automatic switching between the generator and the lithium battery pack; the control cabinet is connected to both the control cabin and the frequency converter; the frequency converter is connected to the alternating-current motor; the alternating-current motor is connected to the decelerator; the decelerator is connected to the propeller; the control cabinet controls, through the frequency converter, the alternating-current motor to rotate; and the alternating-current motor drives the propeller through the decelerator.

Optionally, the remote communications device includes a radar and an antenna; both the radar and the antenna are arranged outside the cabin through an equipment rack; and the equipment rack is further configured to arrange the water-surface photographing device.

Optionally, the power equipment compartment further includes a control panel; and the control panel is connected to the generator, and is configured to display operating parameters of the generator.

The present invention further provides a control method for aquatic ecosystem restoration, applied to the above-mentioned USV for aquatic ecosystem monitoring and restoration, where the method includes the following steps:

obtaining water quality parameters of to-be-detected water, an underwater creature image, and a water-surface creature image, where the water quality parameters include a dissolved oxygen concentration, pH, temperature, turbidity, conductivity, chlorophyll content, blue-green algae content, nitrogen content, phosphorus content, and organic pollutant content;

obtaining a statistical result of survival rates of aquatic organisms in the to-be-detected water according to the underwater creature image and the water-surface creature image;

obtaining an aquatic ecosystem health index of the to-be-detected water according to the water quality parameters and the statistical result of the survival rates of the aquatic organisms;

obtaining an aquatic ecosystem restoration factor according to the water quality parameters and the aquatic ecosystem health index by using a PID control algorithm, where a proportional gain, an integral gain, and a differential gain in the PID algorithm are determined by using a neural network algorithm; and controlling the water treatment equipment compartment to restore the to-be-detected water by using the aquatic ecosystem restoration factor.

Optionally, the obtaining an aquatic ecosystem health index of the to-be-detected water according to the water quality parameters and the statistical result of the survival rates of the aquatic organisms specifically includes:

determining a normalized value of a water eutrophication index according to the water quality parameters:

$$I_1 = \sum_{j=1}^{m} W_j \cdot TLI(j)$$

where $TLI(j)$ represents a normalized value of a $j^{th}$ monitoring index of the water quality parameters; m represents the total number of monitoring indexes corresponding to the water quality parameters; and $W_j$ represents a weight coefficient of the $j^{th}$ monitoring index;

determining a normalized value of a biodiversity index according to the statistical result of the survival rates of the aquatic organisms:

$$I_2 = \sum_{i=1}^{s} \frac{a_i n_i}{N}$$

where s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species; and obtaining the aquatic ecosystem health index of the to-be-detected water according to the normalized value of the water eutrophication index and the normalized value of the biodiversity index:

$$I_{CH} = I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

Compared with the prior art, the present invention has the following beneficial effects:

The present invention proposes a USV for aquatic ecosystem monitoring and restoration. A control cabin, a water-quality monitoring cabin, and a water treatment equipment compartment are arranged inside a cabin of a hull of the USV for aquatic ecosystem monitoring and restoration, and a water-surface photographing device and a remote communications device are arranged outside the cabin; the control cabin is connected to the water-quality monitoring cabin, the water-surface photographing device, and the water treatment equipment compartment; the water-quality monitoring cabin is configured to monitor water quality parameters of to-be-detected water and obtain an underwater creature image; the water-surface photographing device is configured to obtain a water-surface creature image; the water quality parameters include five conventional water quality parameters and eutrophication-based water quality parameters; the eutrophication-based water quality parameters include chlorophyll content, blue-green algae content, nitrogen content, phosphorus content, and organic pollutant content; and the control cabin is configured to receive the water quality parameters, the underwater creature image, and the water-surface creature image, and control the water treatment equipment compartment to restore the to-be-detected water. The USV can implement real-time, automatic, and dynamic aquatic ecosystem monitoring and early warning of the water pollution.

The present invention also proposes a control method for aquatic ecosystem restoration, where an aquatic ecosystem restoration factor is obtained according to water quality parameters and an aquatic ecosystem health index by using a PID control algorithm, and a proportional gain, an integral gain, and a differential gain in the PID algorithm are determined by using a neural network algorithm. In this way, self-cleaning and self-balancing of the aquatic ecosystem can be implemented.

BRIEF DESCRIPTION OF THE DRAWINGS

The present invention is further described in detail with reference to the accompanying drawings.

DETAILED DESCRIPTION

The following clearly and completely describes the technical solutions in the embodiments of the present invention with reference to accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

To make objectives, features, and advantages of the present invention more comprehensible, the following describes the present invention in more detail with reference to accompanying drawings and specific implementations.

Figure 1:
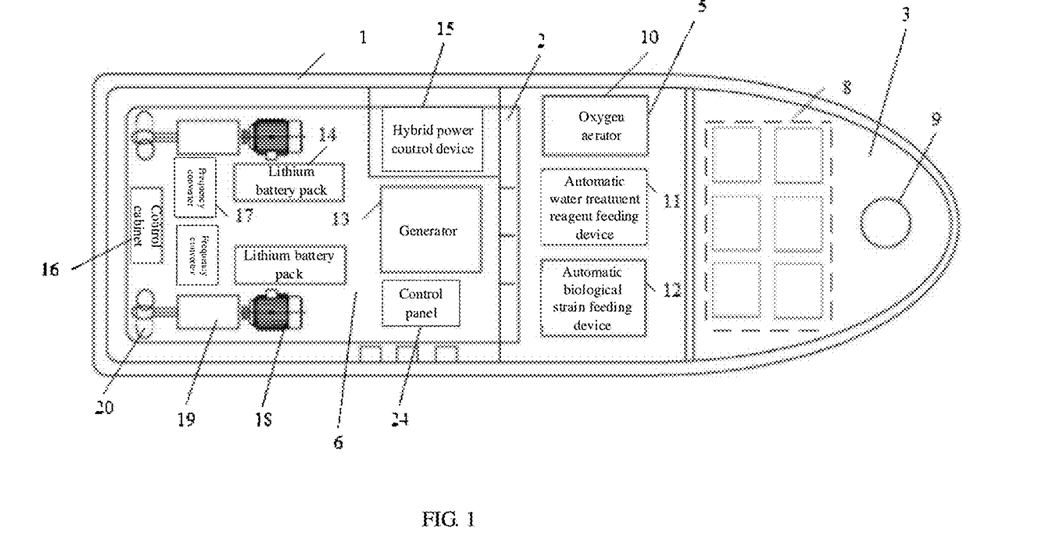
FIG. 1 is a top view of an internal structure of a cabin of a USV for aquatic ecosystem monitoring and restoration according to an embodiment of the present invention.
Figure 2:
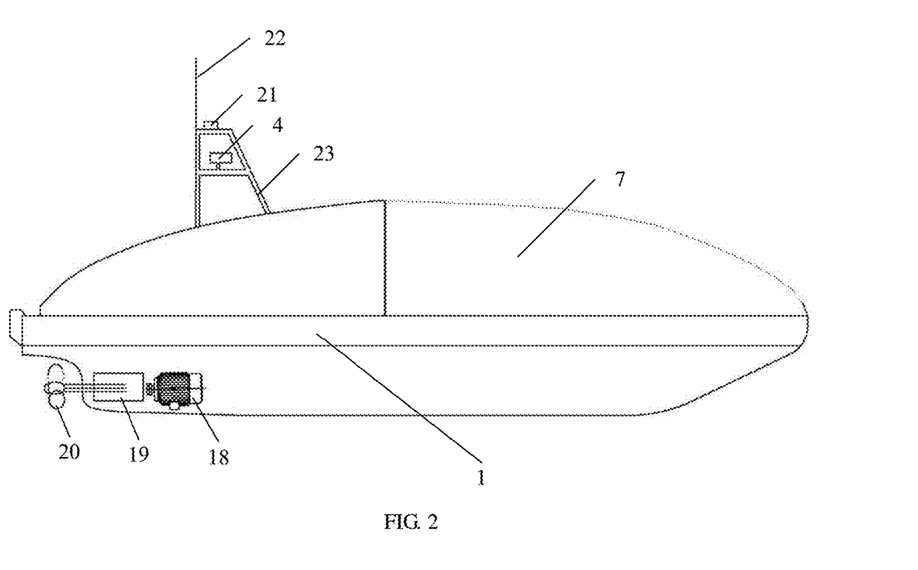
FIG. 2 is a front view of a USV for aquatic ecosystem monitoring and restoration according to an embodiment of the present invention.

FIG. 1 is a top view of an internal structure of a cabin of a USV for aquatic ecosystem monitoring and restoration according to an embodiment of the present invention. FIG. 2 is a front view of a USV for aquatic ecosystem monitoring and restoration according to an embodiment of the present invention.

Referring to FIG. 1 and FIG. 2, the USV for aquatic ecosystem monitoring and restoration in this embodiment includes a hull 1, a control cabin 2, a water-quality monitoring cabin 3, a water-surface photographing device 4, a water treatment equipment compartment 5, and a remote communications device, a power equipment compartment 6, and a solar panel 7. The control cabin 2, the water-quality monitoring cabin 3, the water treatment equipment compartment 5, and the power equipment compartment 6 are arranged inside a cabin of the hull 1, and the water-surface photographing device 4 and the remote communications device are arranged outside the cabin; and the solar panel 7 is connected to the power equipment compartment 6, arranged on the outer surface of the cabin, and configured to charge equipment inside the power equipment compartment 6. In this embodiment, the hull 1 is a mono hull 1 or a twin hull 1 made of aluminum alloy, steel, or a fiberglass material.

The control cabin 2 is connected to the water-quality monitoring cabin 3, the water-surface photographing device 4, and the water treatment equipment compartment 5; the water-quality monitoring cabin 3 is configured to monitor water quality parameters of to-be-detected water and obtain an underwater creature image; the water-surface photographing device 4 is configured to obtain a water-surface creature image; the water quality parameters include five conventional water quality parameters and eutrophication-based water quality parameters; the eutrophication-based water quality parameters include chlorophyll content, blue-green algae content, nitrogen content, phosphorus content, and organic pollutant content; the control cabin 2 is configured to receive the water quality parameters, the underwater creature image, and the water-surface creature image, and control the water treatment equipment compartment 5 to restore the to-be-detected water; the remote communications device is connected to both the water-quality monitoring cabin 3 and the water treatment equipment compartment 5, and is configured to remotely send obtained data; and the power equipment compartment 6 is configured to drive the hull 1.

The water-quality monitoring cabin 3 includes: an aquatic ecosystem analyzer 8, connected to the control cabin 2 and configured to monitor the water quality parameters of the to-be-detected water; and an underwater camera 9, connected to the control cabin 2 and configured to photograph underwater creatures in the to-be-detected water to obtain an underwater creature image. The aquatic ecosystem analyzer 8 includes: a five-parameter water quality analyzer, configured to monitor the five conventional water quality parameters of the to-be-detected water, where the five conventional water quality parameters include a dissolved oxygen concentration, pH, temperature, turbidity, and conductivity; a chlorophyll analyzer, configured to monitor chlorophyll content of the to-be-detected water; a blue-green algae analyzer, configured to monitor blue-green algae content of the to-be-detected water; a COD analyzer, configured to monitor COD content of the to-be-detected water; an ammonia-nitrogen analyzer, configured to monitor ammonia nitrogen content of the to-be-detected water; a total phosphorus analyzer, configured to monitor total phosphorus content of the to-be-detected water; and a total nitrogen analyzer, configured to monitor total nitrogen content of the to-be-detected water.

The water treatment equipment compartment 5 includes: an oxygen aerator 10, connected to the control cabin 2 and configured to provide oxygen gas for the to-be-detected water through micro-nano or conventional aeration; an automatic water treatment agent feeding device 11, connected to the control cabin 2 and configured to feed a water treatment agent to the to-be-detected water; and an automatic water treatment bacteria feeding device 12, connected to the control cabin 2 and configured to feed water treatment bacteria to the to-be-detected water. The oxygen aerator 10 in this embodiment is a micro-nano bubble oxygen aerator, which provides air for water and increases a concentration of dissolved oxygen in the water. Compared with an ordinary aeration device, the micro-nano bubble oxygen aerator has higher efficiency of oxygen gas supply with bubbles staying longer in water, and can also degrade pollutants. The water treatment agent fed by the automatic water treatment agent feeding device 11 is mainly a rapid flocculant and is used for emergency treatment of the water pollution. The water treatment bacteria fed by the automatic water treatment bacteria feeding device 12 include water treatment bacteria for degrading water pollutants and mainly include microbial agents for nitrogen and phosphorus removal, bacteria for degradation of bottom sediment, etc. The water treatment bacteria are used for removal and degradation of nitrogen, phosphorus, or other nutrient elements in eutrophic water.

The power equipment compartment 6 includes a generator 13, a lithium battery pack 14, a hybrid power control device 15, a control cabinet 16, a frequency converter 17, an alternating-current motor 18, a decelerator 19, and a propeller 20; the hybrid power control device 15 is connected to both the generator 13 and the lithium battery pack 14, and is configured to control automatic switching between the generator 13 and the lithium battery pack 14; the control cabinet 16 is connected to both the control cabin 2 and the frequency converter 17; the frequency converter 17 is connected to the alternating-current motor 18; the alternating-current motor 18 is connected to the decelerator 19; the decelerator 19 is connected to the propeller 20; the control cabinet 16 controls, through the frequency converter 17, the alternating-current motor 18 to rotate; and the alternating-current motor 18 drives the propeller 20 through the decelerator 19. Both the generator 13 and the lithium battery pack 14 are connected to electric devices, and are configured to supply power to devices in the hull. The solar panel 7 is connected to the lithium battery pack 14 through a power control manager, and automatically implements charging management. The frequency converter 17 is configured to control a rotational speed of the alternating-current motor 18 to control a cruising speed of the hull 1. The frequency of the frequency converter 17 is provided by the control cabin 2, and the frequency value determines the control of the rotational speed of the motor.

The remote communications device includes a radar 21 and an antenna 22; both the radar 21 and the antenna 22 are arranged outside the cabin through an equipment rack 23; and the equipment rack 23 is further configured to arrange the water-surface photographing device 4.

In an optional implementation, the power equipment compartment 6 further includes a control panel 24; and the control panel is connected to the generator, and is configured to display operating parameters of the generator.

The USV for aquatic ecosystem monitoring and restoration in this embodiment can implement real-time, automatic, and dynamic aquatic ecosystem monitoring and early warning of the water pollution.

The present invention further provides a control method for aquatic ecosystem restoration. The control method is applied to the above USV for aquatic ecosystem monitoring and restoration, and includes the following steps:

Step S1: Obtain water quality parameters of to-be-detected water, an underwater creature image, and a water-surface creature image, where the water quality parameters include a dissolved oxygen concentration, pH, temperature, turbidity, conductivity, chlorophyll content, blue-green algae content, nitrogen content, phosphorus content, and organic pollutant content.

Step S2: Obtain a statistical result of survival rates of aquatic organisms in the to-be-detected water according to the underwater creature image and the water-surface creature image.

Step S3: Obtain an aquatic ecosystem health index of the to-be-detected water according to the water quality parameters and the statistical result of the survival rates of the aquatic organisms.

Step S3 specifically includes:

(1) Determine a normalized value of a water eutrophication index according to the water quality parameters:

$$I_1 = \sum_{j=1}^{m} W_j \cdot TLI(j)$$

where $TLI(j)$ represents a normalized value of a $j^{th}$ monitoring index of the water quality parameters; m represents the total number of monitoring indexes corresponding to the water quality parameters; and $W_j$ represents a weight coefficient of the $j^{th}$ monitoring index.

(2) Determine a normalized value of a biodiversity index according to the statistical result of the survival rates of the aquatic organisms:

$$I_2 = \sum_{i=1}^{s} \frac{a_i n_i}{N}$$

where s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species.

(3) Obtain the aquatic ecosystem health index of the to-be-detected water according to the normalized value of the water eutrophication index and the normalized value of the biodiversity index:

$$I_{CH} = I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

Step S4: Obtain an aquatic ecosystem restoration factor according to the water quality parameters and the aquatic ecosystem health index by using a PID control algorithm, where a proportional gain, an integral gain, and a differential gain in the PID algorithm are determined by using a neural network algorithm.

Step S5: Control the water treatment equipment compartment to restore the to-be-detected water by using the aquatic ecosystem restoration factor.

A specific embodiment of the control method for aquatic ecosystem restoration is provided below.

Figure 3:
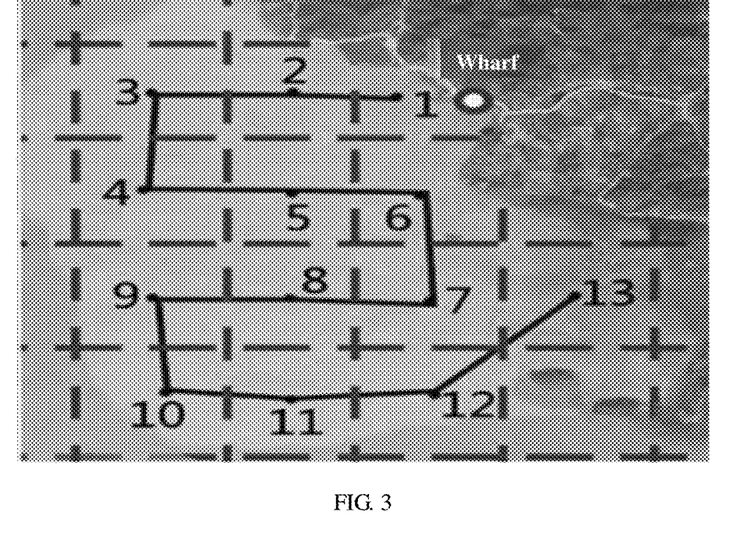
FIG. 3 is a spatial and temporal grid distribution of aquatic ecosystem health indexes according to an embodiment of the present invention.

(1) The USV for aquatic ecosystem monitoring and restoration cruises waters to be operated according to a planned path. As shown in FIG. 3, the waters to be operated are divided into 13 grids. The USV for aquatic ecosystem monitoring and restoration conducts cruising according to a route shown in the figure, and detects water quality in each grid. Detection indexes include a dissolved oxygen concentration, pH, temperature, turbidity, conductivity, chlorophyll content, blue-green algae content, ammonia-nitrogen content, total phosphorus content, total nitrogen content, etc. At the same time, the USV captures a water-surface creature image and an underwater creature image respectively by using an onboard water-surface photographing device and underwater camera.

(2) Conduct image recognition on the water-surface creature image and the underwater creature image. Aquatic organisms include benthic organisms, fish, aquatic plants, etc., and benthic organisms include snails, shellfish, omnivorous shrimps, small omnivorous crabs, etc. A specific recognition method includes: 1). conducting denoising on an image by using a wavelet-based algorithm, to further conduct background subtraction; 2). enhancing the image by using an algorithm for binary-image morphological dilation and erosion; 3). recognizing a target by using a deep neural network algorithm; and 4). collecting statistics on survival rates of aquatic organisms by normal distribution.

(3) Conduct comprehensive aquatic ecosystem health evaluation, where an aquatic ecosystem health index is $I_{CH}$, and its calculation method is as follows:

$I_{CH} = I_1 \cdot W'_1 + I_2 \cdot W'_2$, where $I_1$ represents a normalized value of a water eutrophication index; $I_2$ represents a normalized value of a biodiversity index; $W'_1$ represents a weight coefficient corresponding to the normalized value of the water eutrophication index; and $W'_2$ represents a weight coefficient corresponding to the normalized value of the biodiversity index; and $W'_1$ and $W'_2$ are obtained based on empirical values and unsupervised learning of an ecosystem model.

Where, $$I_1 = \sum_{j=1}^{m} W_j \cdot TLI(j),$$

where TLI(j) represents a normalized value of a $j^{th}$ monitoring index of the water quality parameters; m represents the total number of monitoring indexes corresponding to the water quality parameters; $W_j$ represents a weight coefficient of the $j^{th}$ monitoring index; and $W_j$ is obtained based on an empirical value and unsupervised learning of the ecosystem model.

Where, $$I_2 = \sum_{i=1}^{s} \frac{a_i n_i}{N},$$

where s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species.

A specific embodiment of the step is provided below:

Calculation of the normalized value $I_1$ of the water eutrophication index: Main water eutrophication parameters such as dissolved oxygen DO, ammonia nitrogen $NH_3$—N, total phosphorus TP, total nitrogen TN, and COD are selected as water-quality monitoring indexes, all the values are set to 0.8, and their coefficients are 0.15, 0.2, 0.2, 0.3, and 0.15, respectively. In this case, $I_1$=0.8×0.15+0.8×0.2+0.8×0.2+0.8×0.3+0.8×0.15=0.8.

Calculation of the normalized value $I_2$ of the biodiversity index: N=10, $n_1$=5, $n_2$=5, s=2, $a_1$=$a_2$=0.5, and a calculation result is $I_2$=0.5.

Finally, $I_{CH}$=0.8×0.5+0.5×0.5=0.65 is calculated. A threshold of the aquatic ecosystem health index is set to 0.5. If the aquatic ecosystem health index exceeds 0.5, an ecological restoration process shall be immediately started.

Aquatic ecosystem health statuses corresponding to aquatic ecosystem health indexes are shown in Table 1.

TABLE 1

| $I_{CH}$ index | Status description |
|---|---|
| ≤0.35 | Very healthy |
| 0.35-0.45 | Healthy |
| 0.45-0.55 | General |
| 0.55-0.65 | Lightly polluted |
| 0.65-0.75 | Moderately polluted |
| ≥0.75 | Severely polluted |

(4) Conduct spatial and temporal grid distribution of aquatic ecosystem health indexes. The spatial and temporal grid distribution of aquatic ecosystem health indexes is based on values of the aquatic ecosystem health index $I_{CH}$ calculated in step (3). An aquatic ecosystem health status is provided by drawing according to grids in the waters to be operated. Each grid interval is 10-50 m. Aquatic ecosystem health indexes corresponding to the grids are represented by colors of different depths, and a darker color indicates a worse health status.

(5) Conduct intelligent aquatic ecosystem restoration (autonomous cruising is conducted according to the grid distribution diagram).

Figure 4:
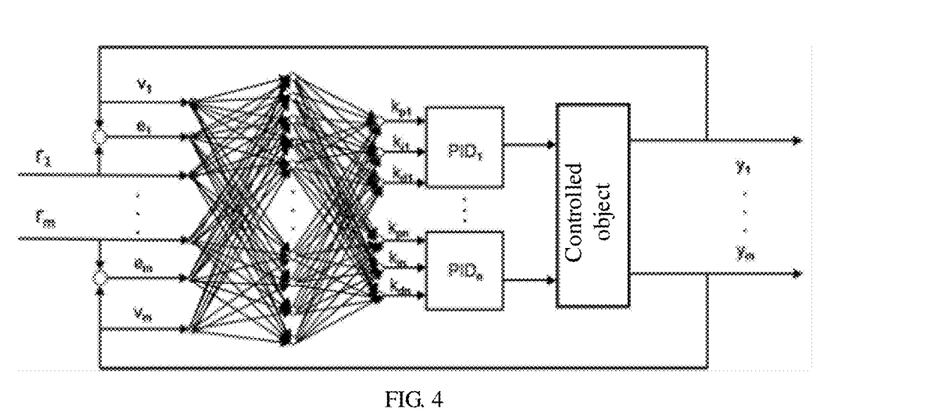
FIG. 4 is a schematic structural diagram of an intelligent controller for ecological restoration according to an embodiment of the present invention.

An ecological health threshold is set for each grid according to the spatial and temporal grid distribution of aquatic ecosystem health indexes in step (4). Once an ecological health index exceeds a threshold 0.5, the intelligent ecological restoration process will be started. A specific restoration process is as follows: FIG. 4 is a schematic structural diagram of an intelligent controller for ecological restoration according to an embodiment of the present invention. The controller integrates an artificial neural network algorithm and closed-loop PID control. The input of the controller is $r_i$-$r_m$, and respectively includes water eutrophication parameters such as a dissolved oxygen concentration, pH, temperature, turbidity, conductivity, chlorophyll content, blue-green algae content, ammonia-nitrogen content, total phosphorus content, total nitrogen content, and an aquatic ecosystem health index of aquatic organisms.

Figure 5:
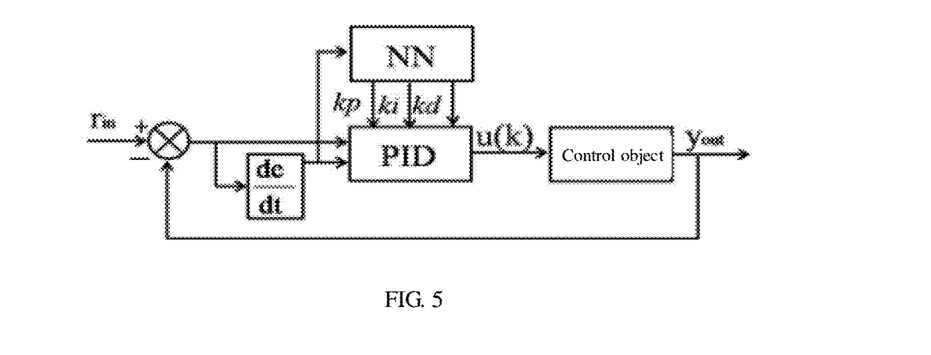
FIG. 5 is a schematic diagram of a control method implemented by a single controller according to an embodiment of the present invention.

Specifically, a control method implemented by each controller is shown in FIG. 5. The intelligent controller includes two parts: a classical PID controller and a neural network algorithm. The classical PID controller obtains a regulator output u(k) according to an intelligent control algorithm by using an error between an input $r_{in}$ and output $y_{out}$, an error variation de/dt, and parameters ki, kp, and kd adjusted online by using the neural network algorithm, and then obtains the output $y_{out}$ of a system according to a transfer function of a control object, so as to implement direct closed-loop control on a controlled object. The neural network algorithm part outputs, through self-learning of a neural network and weight coefficient adjustment, PID controller parameters ki, kp, and kd corresponding to certain optimal control according to an operating status of the system and a certain optimum water quality index.

A PID controller parameter tuning method based on the neural network mainly includes the following several steps:

(1) Determine a network layer structure of a neural network model. An output layer is corresponding to three adjustable parameters, and the network layer structure must include more than three layers. Therefore, only the number of input layers and hidden layers need to be determined, a weight of each layer needs to be initialized, and a learning rate and an inertia coefficient need to be selected.

(2) Obtain an input and output signal of water quality parameters by sampling, and calculate an error between a given value and an input value.

(3) Calculate an input and output value of each layer of neural network.

(4) Calculate an output u(k) of the PID controller.

(5) Adjust the weight coefficient through online learning of the neural network, to implement self-adjustment of three parameters of the PID controller.

(6) Set k=k+1, and return to (1).

According to the control method for aquatic ecosystem restoration in this embodiment, automatic recognition is conducted on images obtained by the water-surface photographing device and the underwater camera; and the probability distribution of aquatic organisms is calculated by a statistical algorithm, to further obtain a growth status and an ecological factor of the aquatic organisms. In the intelligent control method for aquatic ecosystem restoration, closed-loop control based on the neural network is conducted on ecosystem factors, where on-line monitoring parameters such as an aquatic ecosystem factor and an aquatic environment factor are used as a network input, an aquatic ecosystem restoration factor is used as an output parameter, the output parameter is used as a feedback coefficient of a closed-loop control system for aquatic ecosystem restoration. In this way, self-cleaning and self-balancing of the aquatic ecosystem can be finally implemented.

The embodiments of the present invention are described in detail above with reference to the accompanying drawings, but the present invention is not limited to the above embodiments. Within the knowledge of a person of ordinary skill in the art, various variations can also be made without departing from the spirit of the present invention.

What is claimed is:

1. An Unmanned Surface Vehicle (USV) for aquatic ecosystem monitoring and restoration, comprising a hull, a control cabin, a water-quality monitoring cabin, a water-surface photographing device, a water treatment equipment compartment, and a remote communications device, wherein the control cabin, the water-quality monitoring cabin, and the water treatment equipment compartment are arranged inside a cabin of the hull, and the water-surface photographing device and the remote communications device are arranged outside the cabin; and the control cabin is connected to the water-quality monitoring cabin, the water-surface photographing device, and the water treatment equipment compartment; the water-quality monitoring cabin is configured to monitor water quality parameters of to-be-detected water and obtain an underwater creature image; the water-surface photographing device is configured to obtain a water-surface creature image; the water quality parameters comprise five conventional water quality parameters and eutrophication-based water quality parameters; the eutrophication-based water quality parameters comprise chlorophyll content, blue-green algae content, nitrogen content, phosphorus content, and organic pollutant content; the control cabin is configured to receive the water quality parameters, the underwater creature image, and the water-surface creature image, and control the water treatment equipment compartment to restore the to-be-detected water; and the remote communications device is connected to both the water-quality monitoring cabin and the water treatment equipment compartment, and is configured to remotely send obtained data.

2. The USV for aquatic ecosystem monitoring and restoration according to claim 1, wherein the water-quality monitoring cabin comprises:

an aquatic ecosystem analyzer, connected to the control cabin and configured to monitor the water quality parameters of the to-be-detected water; and an underwater camera, connected to the control cabin and configured to photograph underwater creatures in the to-be-detected water to obtain an underwater creature image.

3. The USV for aquatic ecosystem monitoring and restoration according to claim 2, wherein the aquatic ecosystem analyzer comprises:

a five-parameter water quality analyzer, configured to monitor the five conventional water quality parameters of the to-be-detected water, wherein the five conventional water quality parameters comprise a dissolved oxygen concentration, pH, temperature, turbidity, and conductivity;

a chlorophyll analyzer, configured to monitor chlorophyll content of the to-be-detected water;

a blue-green algae analyzer, configured to monitor blue-green algae content of the to-be-detected water;

a COD analyzer, configured to monitor COD content of the to-be-detected water;

an ammonia-nitrogen analyzer, configured to monitor ammonia nitrogen content of the to-be-detected water;

a total phosphorus analyzer, configured to monitor total phosphorus content of the to-be-detected water; and a total nitrogen analyzer, configured to monitor total nitrogen content of the to-be-detected water.

4. The USV for aquatic ecosystem monitoring and restoration according to claim 1, wherein the water treatment equipment compartment comprises:

an oxygen aerator, connected to the control cabin and configured to provide oxygen gas for the to-be-detected water through micro-nano or conventional aeration;

an automatic water treatment agent feeding device, connected to the control cabin and configured to feed a water treatment agent to the to-be-detected water; and an automatic water treatment bacteria feeding device, connected to the control cabin and configured to feed water treatment bacteria to the to-be-detected water.

5. The USV for aquatic ecosystem monitoring and restoration according to claim 1, further comprising:

a power equipment compartment, arranged inside the cabin and configured to drive the hull; and a solar panel, connected to the power equipment compartment, arranged on the outer surface of the cabin, and configured to charge equipment in the power equipment compartment.

6. The USV for aquatic ecosystem monitoring and restoration according to claim 5, wherein the power equipment compartment comprises a generator, a lithium battery pack, a hybrid power control device, a control cabinet, a frequency converter, an alternating-current motor, a decelerator, and a propeller; and the hybrid power control device is connected to both the generator and the lithium battery pack, and is configured to control automatic switching between the generator and the lithium battery pack; the control cabinet is connected to both the control cabin and the frequency converter; the frequency converter is connected to the alternating-current motor; the alternating-current motor is connected to the decelerator; the decelerator is connected to the propeller; the control cabinet controls, through the frequency converter, the alternating-current motor to rotate;

and the alternating-current motor drives the propeller through the decelerator.

7. The USV for aquatic ecosystem monitoring and restoration according to claim 1, wherein the remote communications device comprises a radar and an antenna; both the radar and the antenna are arranged outside the cabin through an equipment rack; and the equipment rack is further configured to arrange the water-surface photographing device.

8. The USV for aquatic ecosystem monitoring and restoration according to claim 5, wherein the power equipment compartment further comprises a control panel; and the control panel is connected to the generator, and is configured to display operating parameters of the generator.

9. A control method for aquatic ecosystem restoration, applied to the USV for aquatic ecosystem monitoring and restoration according to claim 1, wherein the method comprises the following steps:
   obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;
   obtaining a statistical result of survival rates of aquatic organisms in the to-be-detected water according to the underwater creature image and the water-surface creature image;
   obtaining an aquatic ecosystem health index of the to-be-detected water according to the water quality parameters and the statistical result of the survival rates of the aquatic organisms;
   obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and
   controlling the water treatment equipment compartment to restore the to-be-detected water by using the aquatic ecosystem restoration factor.

10. A control method for aquatic ecosystem restoration, applied to the USV for aquatic ecosystem monitoring and restoration according to claim 2, wherein the method comprises the following steps:
   obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;
   obtaining a statistical result of survival rates of aquatic organisms in the to-be-detected water according to the underwater creature image and the water-surface creature image;
   obtaining an aquatic ecosystem health index of the to-be-detected water according to the water quality parameters and the statistical result of the survival rates of the aquatic organisms;
   obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and
   controlling the water treatment equipment compartment to restore the to-be-detected water by using the aquatic ecosystem restoration factor.

11. A control method for aquatic ecosystem restoration, applied to the USV for aquatic ecosystem monitoring and restoration according to claim 3, wherein the method comprises the following steps:
   obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;
   obtaining a statistical result of survival rates of aquatic organisms in the to-be-detected water according to the underwater creature image and the water-surface creature image;
   obtaining an aquatic ecosystem health index of the to-be-detected water according to the water quality parameters and the statistical result of the survival rates of the aquatic organisms;
   obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and
   controlling the water treatment equipment compartment to restore the to-be-detected water by using the aquatic ecosystem restoration factor.

12. A control method for aquatic ecosystem restoration, applied to the USV for aquatic ecosystem monitoring and restoration according to claim 4, wherein the method comprises the following steps:
   obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;
   obtaining a statistical result of survival rates of aquatic organisms in the to-be-detected water according to the underwater creature image and the water-surface creature image;
   obtaining an aquatic ecosystem health index of the to-be-detected water according to the water quality parameters and the statistical result of the survival rates of the aquatic organisms;
   obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and
   controlling the water treatment equipment compartment to restore the to-be-detected water by using the aquatic ecosystem restoration factor.

13. A control method for aquatic ecosystem restoration, applied to the USV for aquatic ecosystem monitoring and restoration according to claim 5, wherein the method comprises the following steps:
   obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;
   obtaining a statistical result of survival rates of aquatic organisms in the to-be-detected water according to the underwater creature image and the water-surface creature image;
   obtaining an aquatic ecosystem health index of the to-be-detected water according to the water quality parameters and the statistical result of the survival rates of the aquatic organisms;
   obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and controlling the water treatment equipment compartment to restore the to-be-detected water by using the aquatic ecosystem restoration factor.

14. A control method for aquatic ecosystem restoration, applied to the USV for aquatic ecosystem monitoring and restoration according to claim 6, wherein the method comprises the following steps:

obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;

obtaining a statistical result of survival rates of aquatic organisms in the to-be-detected water according to the underwater creature image and the water-surface creature image;

obtaining an aquatic ecosystem health index of the to-be-detected water according to the water quality parameters and the statistical result of the survival rates of the aquatic organisms;

obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and controlling the water treatment equipment compartment to restore the to-be-detected water by using the aquatic ecosystem restoration factor.

15. A control method for aquatic ecosystem restoration, applied to the USV for aquatic (New) ecosystem monitoring and restoration according to claim 7, wherein the method comprises the following steps:

obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;

obtaining a statistical result of survival rates of aquatic organisms in the to-be-detected water according to the underwater creature image and the water-surface creature image;

obtaining an aquatic ecosystem health index of the to-be-detected water according to the water quality parameters and the statistical result of the survival rates of the aquatic organisms;

obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and controlling the water treatment equipment compartment to restore the to-be-detected water by using the aquatic ecosystem restoration factor.

16. A control method for aquatic ecosystem restoration, applied to the USV for aquatic ecosystem monitoring and restoration according to claim 8, wherein the method comprises the following steps:

obtaining water quality parameters of to-be-detected water, an underwater creature image, and a water-surface creature image, wherein the water quality parameters comprise a dissolved oxygen concentration, pH, temperature, turbidity, conductivity, chlorophyll content, blue-green algae content, nitrogen content, phosphorus content, and organic pollutant content;

obtaining a statistical result of survival rates of aquatic organisms in the to-be-detected water according to the underwater creature image and the water-surface creature image;

obtaining an aquatic ecosystem health index of the to-be-detected water according to the water quality parameters and the statistical result of the survival rates of the aquatic organisms;

obtaining an aquatic ecosystem restoration factor according to the water quality parameters and the aquatic ecosystem health index by using a PID control algorithm, wherein a proportional gain, an integral gain, and a differential gain in the PID algorithm are determined by using a neural network algorithm; and controlling the water treatment equipment compartment to restore the to-be-detected water by using the aquatic ecosystem restoration factor.

17. The control method for aquatic ecosystem restoration according to claim 9, wherein the obtaining an aquatic ecosystem health index of the to-be-detected water according to the water quality parameters and the statistical result of the survival rates of the aquatic organisms specifically comprises:

determining a normalized value of a water eutrophication index according to the water quality parameters:

$$I_1 = \sum_{j=1}^{m} W_j \cdot TLI(j)$$

wherein $TLI(j)$ represents a normalized value of a $j^{th}$ monitoring index of the water quality parameters; m represents the total number of monitoring indexes corresponding to the water quality parameters; and $W_j$ represents a weight coefficient of the $j^{th}$ monitoring index;

determining a normalized value of a biodiversity index according to the statistical result of the survival rates of the aquatic organisms:

$$I_2 = \sum_{i=1}^{s} \frac{a_i n_i}{N}$$

wherein s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species; and obtaining the aquatic ecosystem health index of the to-be-detected water according to the normalized value of the water eutrophication index and the normalized value of the biodiversity index:

$$I_{CH} = I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

18. The control method for aquatic ecosystem restoration according to claim 10, wherein the obtaining an aquatic ecosystem health index of the to-be-detected water according to the water quality parameters and the statistical result of the survival rates of the aquatic organisms specifically comprises:

determining a normalized value of a water eutrophication index according to the water quality parameters:

$$I_1 = \sum_{j=1}^{m} W_j \cdot TLI(j)$$

wherein TLI(j) represents a normalized value of a $j^{th}$ monitoring index of the water quality parameters; m represents the total number of monitoring indexes corresponding to the water quality parameters; and $W_j$ represents a weight coefficient of the $j^{th}$ monitoring index;

determining a normalized value of a biodiversity index according to the statistical result of the survival rates of the aquatic organisms:

$$I_2 = \sum_{i=1}^{s} \frac{a_i n_i}{N}$$

wherein s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species; and obtaining the aquatic ecosystem health index of the to-be-detected water according to the normalized value of the water eutrophication index and the normalized value of the biodiversity index:

$$I_{CH} = I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

19. The control method for aquatic ecosystem restoration according to claim 11 wherein the obtaining an aquatic ecosystem health index of the to-be-detected water according to the water quality parameters and the statistical result of the survival rates of the aquatic organisms specifically comprises:

determining a normalized value of a water eutrophication index according to the water quality parameters:

$$I_1 = \sum_{j=1}^{m} W_j \cdot TLI(j)$$

wherein TLI(j) represents a normalized value of a $j^{th}$ monitoring index of the water quality parameters; m represents the total number of monitoring indexes corresponding to the water quality parameters; and $W_j$ represents a weight coefficient of the $j^{th}$ monitoring index;

determining a normalized value of a biodiversity index according to the statistical result of the survival rates of the aquatic organisms:

$$I_2 = \sum_{i=1}^{s} \frac{a_i n_i}{N}$$

wherein s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species; and obtaining the aquatic ecosystem health index of the to-be-detected water according to the normalized value of the water eutrophication index and the normalized value of the biodiversity index:

$$I_{CH} = I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

20. The control method for aquatic ecosystem restoration according to claim 12, wherein the obtaining an aquatic ecosystem health index of the to-be-detected water according to the water quality parameters and the statistical result of the survival rates of the aquatic organisms specifically comprises:

determining a normalized value of a water eutrophication index according to the water quality parameters:

$$I_1 = \sum_{j=1}^{m} W_j \cdot TLI(j)$$

wherein TLI(j) represents a normalized value of a $j^{th}$ monitoring index of the water quality parameters; m represents the total number of monitoring indexes corresponding to the water quality parameters; and $W_j$ represents a weight coefficient of the $j^{th}$ monitoring index;

determining a normalized value of a biodiversity index according to the statistical result of the survival rates of the aquatic organisms:

$$I_2 = \sum_{i=1}^{s} \frac{a_i n_i}{N}$$

wherein s represents the number of species of the organisms; $a_i$ represents a tolerance value of an $i^{th}$ species of organism; $a_i$ is obtained according to the statistical result of the survival rates of the aquatic organisms; $n_i$ represents the number of organisms of the $i^{th}$ species; and N represents the total number of organisms of all species; and obtaining the aquatic ecosystem health index of the to-be-detected water according to the normalized value of the water eutrophication index and the normalized value of the biodiversity index:

$$I_{CH}=I_1 \cdot W'_1 + I_2 \cdot W'_2$$

where $W'_1$ represents a weight coefficient corresponding to the normalized value of the water eutrophication index; and $W'_2$ represents a weight coefficient corresponding to the normalized value of the biodiversity index.

\* \* \* \* \*